(12) United States Patent
Oda

(10) Patent No.: US 8,257,247 B2
(45) Date of Patent: Sep. 4, 2012

(54) ENDOSCOPE INSERTION SHAPE DETECTING DEVICE

(75) Inventor: Tomohiko Oda, Kawagoe (JP)

(73) Assignee: Olympus Medical Systems Corp., Tokyo (JP)

( * ) Notice: Subject to any disclaimer, the term of this patent is extended or adjusted under 35 U.S.C. 154(b) by 1264 days.

(21) Appl. No.: 11/810,583

(22) Filed: Jun. 6, 2007

(65) Prior Publication Data

US 2008/0009714 A1    Jan. 10, 2008

(30) Foreign Application Priority Data

Jun. 12, 2006    (JP) ................. 2006-162919

(51) Int. Cl.
- A61B 1/00    (2006.01)
- A61B 1/04    (2006.01)
- A61B 5/05    (2006.01)

(52) U.S. Cl. .................. 600/117; 600/145; 600/424
(58) Field of Classification Search .................. 600/117, 600/145, 109, 424
See application file for complete search history.

(56) References Cited

U.S. PATENT DOCUMENTS

| | | | | |
|---|---|---|---|---|
| 5,957,833 A * | 9/1999 | Shan | .................. | 600/117 |
| 5,997,473 A * | 12/1999 | Taniguchi et al. | ............ | 600/117 |
| 6,059,718 A * | 5/2000 | Taniguchi et al. | ............ | 600/117 |
| 6,203,493 B1 * | 3/2001 | Ben-Haim | .................. | 600/117 |
| 6,248,074 B1 * | 6/2001 | Ohno et al. | .................. | 600/463 |
| 6,432,041 B1 * | 8/2002 | Taniguchi et al. | ............ | 600/118 |
| 6,589,163 B2 * | 7/2003 | Aizawa et al. | ................ | 600/118 |
| 6,745,065 B2 * | 6/2004 | Niwa et al. | .................. | 600/424 |
| 6,773,394 B2 * | 8/2004 | Taniguchi et al. | ............ | 600/117 |
| 6,846,286 B2 * | 1/2005 | Suzuki et al. | ................ | 600/145 |
| 6,981,941 B2 * | 1/2006 | Whitman et al. | ................ | 600/1 |
| 7,144,367 B2 * | 12/2006 | Chen et al. | .................. | 600/117 |
| 7,599,730 B2 * | 10/2009 | Hunter et al. | ................ | 600/424 |
| 7,653,426 B2 * | 1/2010 | Yatsuo et al. | ................ | 600/423 |
| 7,871,370 B2 * | 1/2011 | Sugimoto | .................. | 600/117 |
| 2002/0169361 A1 * | 11/2002 | Taniguchi et al. | ............ | 600/117 |
| 2003/0055317 A1 * | 3/2003 | Taniguchi et al. | ............ | 600/117 |
| 2003/0060678 A1 * | 3/2003 | Watai et al. | .................. | 600/109 |
| 2004/0116775 A1 * | 6/2004 | Taniguchi et al. | ............ | 600/117 |
| 2005/0228221 A1 * | 10/2005 | Hirakawa | .................. | 600/101 |
| 2007/0066866 A1 * | 3/2007 | Noguchi et al. | ............ | 600/102 |

(Continued)

FOREIGN PATENT DOCUMENTS

EP    1 504 712 A1    2/2005

(Continued)

*Primary Examiner* — Philip R Smith
*Assistant Examiner* — William Chou
(74) *Attorney, Agent, or Firm* — Scully, Scott, Murphy & Presser, P.C.

(57) ABSTRACT

An endoscope insertion shape detecting device of the present invention comprises an insertion shape detection portion for detecting an insertion shape of an endoscope insertion portion, an insertion shape image generation portion for generating an insertion shape figure of the endoscope insertion portion according to the insertion shape, a marking processing portion for carrying out a control to add a mark to the insertion shape figure for output as a control for the insertion shape image generation portion in a first observation for the subject, a memory portion for storing subject information, the insertion shape figure, and information on a position to which the mark is added in the insertion shape figure, and a position detection information output portion for outputting position detection information when a distal end portion of the insertion shape figure overlaps the mark position information in second observation made for the same subject.

24 Claims, 8 Drawing Sheets

U.S. PATENT DOCUMENTS

| | | | |
|---|---|---|---|
| 2007/0208252 A1* | 9/2007 | Makower | 600/424 |
| 2007/0232896 A1* | 10/2007 | Gilboa et al. | 600/424 |
| 2008/0171934 A1* | 7/2008 | Greenan et al. | 600/411 |
| 2009/0156895 A1* | 6/2009 | Higgins et al. | 600/104 |
| 2009/0203989 A1* | 8/2009 | Burnside et al. | 600/409 |
| 2010/0210938 A1* | 8/2010 | Verard et al. | 600/424 |
| 2011/0060214 A1* | 3/2011 | Makower | 600/424 |

FOREIGN PATENT DOCUMENTS

| | | |
|---|---|---|
| EP | 1 632 168 A1 | 3/2006 |
| JP | 11-104072 | 4/1999 |
| WO | WO 2006/060613 A1 | 6/2006 |

\* cited by examiner

ENDOSCOPE INSERTION SHAPE DETECTING DEVICE

This application claims benefit of Japanese Applications No. 2006-162919 filed on Jun. 12, 2006, the contents of which are incorporated by this reference.

BACKGROUND OF THE INVENTION

1. Field of the Invention

The present invention relates to an endoscope insertion shape detecting device and particularly to an endoscope insertion shape detecting device which can generate an insertion shape figure of an endoscope insertion portion.

2. Description of the Related Art

An endoscope has been widely used in the medical field, industrial field and the like. Also, the endoscope is used for observation or various treatments for a portion, a tissue and the like in a body cavity of a living body, which is an affected portion in the medical field, for example.

Particularly, when an endoscope is inserted from an anus side of a living body for observation and various treatments for a lower digestive tract, in order to smoothly insert an insertion portion of the endoscope into the bent body cavity, an endoscope insertion shape detecting device capable of detection of a position, a bent state and the like of the insertion portion within the body cavity is used together with the endoscope.

As a system having a configuration supporting observation using the endoscope, a medical support system in the Japanese Unexamined Patent Application Publication No. 11-104072 is proposed, for example.

SUMMARY OF THE INVENTION

A first endoscope insertion shape detecting device in the present invention comprises an insertion shape detection portion for detecting an insertion shape of an endoscope insertion portion provided with an image pickup portion at the distal end portion, which can pick up an image of a photographic subject existing inside a subject; an insertion shape image generation portion for generating an insertion shape figure of the endoscope insertion portion according to the insertion shape; a marking processing portion for carrying out a control to add a mark to a portion corresponding to the distal end portion of the insertion shape figure for output as a control for the insertion shape image generation portion when an instruction to obtain a still image according to the image of the photographic subject is detected in a first observation for the subject; a memory portion for storing information associated with subject information, which is information relating to the subject, the insertion shape figure, mark position information, which is information of a position to which the mark is added in the insertion shape figure as observation information of the first observation; and a position detection information output portion for outputting position detection information indicating that the distal end portion is reaching the location where the instruction is made in the first observation when a portion corresponding to the distal end portion of the insertion shape figure overlaps the mark position information in second observation made after the first observation made for the same subject.

A second endoscope insertion shape detecting device in the present invention further comprises a magnetic field detection portion for detecting a magnetic field emitted by a plurality of magnetic-field generation elements arranged at the endoscope insertion portion and outputting a magnetic field signal corresponding to the intensity of the magnetic field in the first endoscope insertion shape detecting device, and the insertion shape detection portion estimates a position of each magnetic-field generation element on the basis of the magnetic field signal outputted from the magnetic field detection portion and detects the insertion shape of the endoscope insertion portion on the basis of the estimation result.

In a third endoscope insertion shape detecting device in the present invention, according to the first endoscope insertion shape detecting device, when the position detection information output portion detects that information of a portion where time was required for insertion of the endoscope insertion portion is stored in the memory portion as the observation information, the position detection information output portion outputs position detection information indicating that the distal end portion is reaching the portion.

In a fourth endoscope insertion shape detecting device in the present invention, according to the first endoscope insertion shape detecting device, when the position detection information output portion detects according to the second observation that information of a portion where the endoscope insertion portion forms a loop shape is stored in the memory portion as the observation information, the position detection information output portion outputs position detection information indicating that the distal end portion is reaching the portion.

In a fifth endoscope insertion shape detecting device in the present invention, according to the first endoscope insertion shape detecting device, the position detection information output portion determines in the second observation if the subject to be a target of the second observation is the same as the subject to be the target of the first observation by referring to the subject information held by the observation information stored in the memory portion.

In a sixth endoscope insertion shape detecting device in the present invention, according to the second endoscope insertion shape detecting device, the position detection information output portion determines in the second observation if the subject to be a target of the second observation is the same as the subject to be the target of the first observation by referring to the subject information held by the observation information stored in the memory portion.

In a seventh endoscope insertion shape detecting device in the present invention, according to the third endoscope insertion shape detecting device, the position detection information output portion determines in the second observation if the subject to be a target of the second observation is the same as the subject to be the target of the first observation by referring to the subject information held by the observation information stored in the memory portion.

In an eighth endoscope insertion shape detecting device in the present invention, according to the fourth endoscope insertion shape detecting device, the position detection information output portion determines in the second observation if the subject to be a target of the second observation is the same as the subject to be the target of the first observation by referring to the subject information held by the observation information stored in the memory portion.

In a ninth endoscope insertion shape detecting device in the present invention, according to the first endoscope insertion shape detecting device, the position detection information is displayed as predetermined notification information in a display portion on which an endoscopic image is displayed on the basis of the image of the photographic subject.

In a tenth endoscope insertion shape detecting device in the present invention, according to the second endoscope insertion shape detecting device, the position detection information is displayed as predetermined notification information in a display portion on which an endoscopic image is displayed on the basis of the image of the photographic subject.

In an eleventh endoscope insertion shape detecting device in the present invention, according to the third endoscope insertion shape detecting device, the position detection information is displayed as predetermined notification information in a display portion on which an endoscopic image is displayed on the basis of the image of the photographic subject.

In a twelfth endoscope insertion shape detecting device in the present invention, according to the fourth endoscope insertion shape detecting device, the position detection information is displayed as predetermined notification information in a display portion on which an endoscopic image is displayed on the basis of the image of the photographic subject.

In a thirteenth endoscope insertion shape detecting device in the present invention, according to the fifth endoscope insertion shape detecting device, the position detection information is displayed as predetermined notification information in a display portion on which an endoscopic image is displayed on the basis of the image of the photographic subject.

In a fourteenth endoscope insertion shape detecting device in the present invention, according to the sixth endoscope insertion shape detecting device, the position detection information is displayed as predetermined notification information in a display portion on which an endoscopic image is displayed on the basis of the image of the photographic subject.

In a fifteenth endoscope insertion shape detecting device in the present invention, according to the seventh endoscope insertion shape detecting device, the position detection information is displayed as predetermined notification information in a display portion on which an endoscopic image is displayed on the basis of the image of the photographic subject.

In a sixteenth endoscope insertion shape detecting device in the present invention, according to the eighth endoscope insertion shape detecting device, the position detection information is displayed as predetermined notification information in a display portion on which an endoscopic image is displayed on the basis of the image of the photographic subject.

In a seventeenth endoscope insertion shape detecting device in the present invention, according to the ninth endoscope insertion shape detecting device, the predetermined notification information is information having at least one of symbols and messages.

In an eighteenth endoscope insertion shape detecting device in the present invention, according to the tenth endoscope insertion shape detecting device, the predetermined notification information is information having at least one of symbols and messages.

In a nineteenth endoscope insertion shape detecting device in the present invention, according to the eleventh endoscope insertion shape detecting device, the predetermined notification information is information having at least one of symbols and messages.

In a twentieth endoscope insertion shape detecting device in the present invention, according to the twelfth endoscope insertion shape detecting device, the predetermined notification information is information having at least one of symbols and messages.

In a twenty-first endoscope insertion shape detecting device in the present invention, according to the thirteenth endoscope insertion shape detecting device, the predetermined notification information is information having at least one of symbols and messages.

In a twenty-second endoscope insertion shape detecting device in the present invention, according to the fourteenth endoscope insertion shape detecting device, the predetermined notification information is information having at least one of symbols and messages.

In a twenty-third endoscope insertion shape detecting device in the present invention, according to the fifteenth endoscope insertion shape detecting device, the predetermined notification information is information having at least one of symbols and messages.

In a twenty-fourth endoscope insertion shape detecting device in the present invention, according to the sixteenth endoscope insertion shape detecting device, the predetermined notification information is information having at least one of symbols and messages.

DETAILED DESCRIPTION OF PREFERRED EMBODIMENTS

Figure 1:
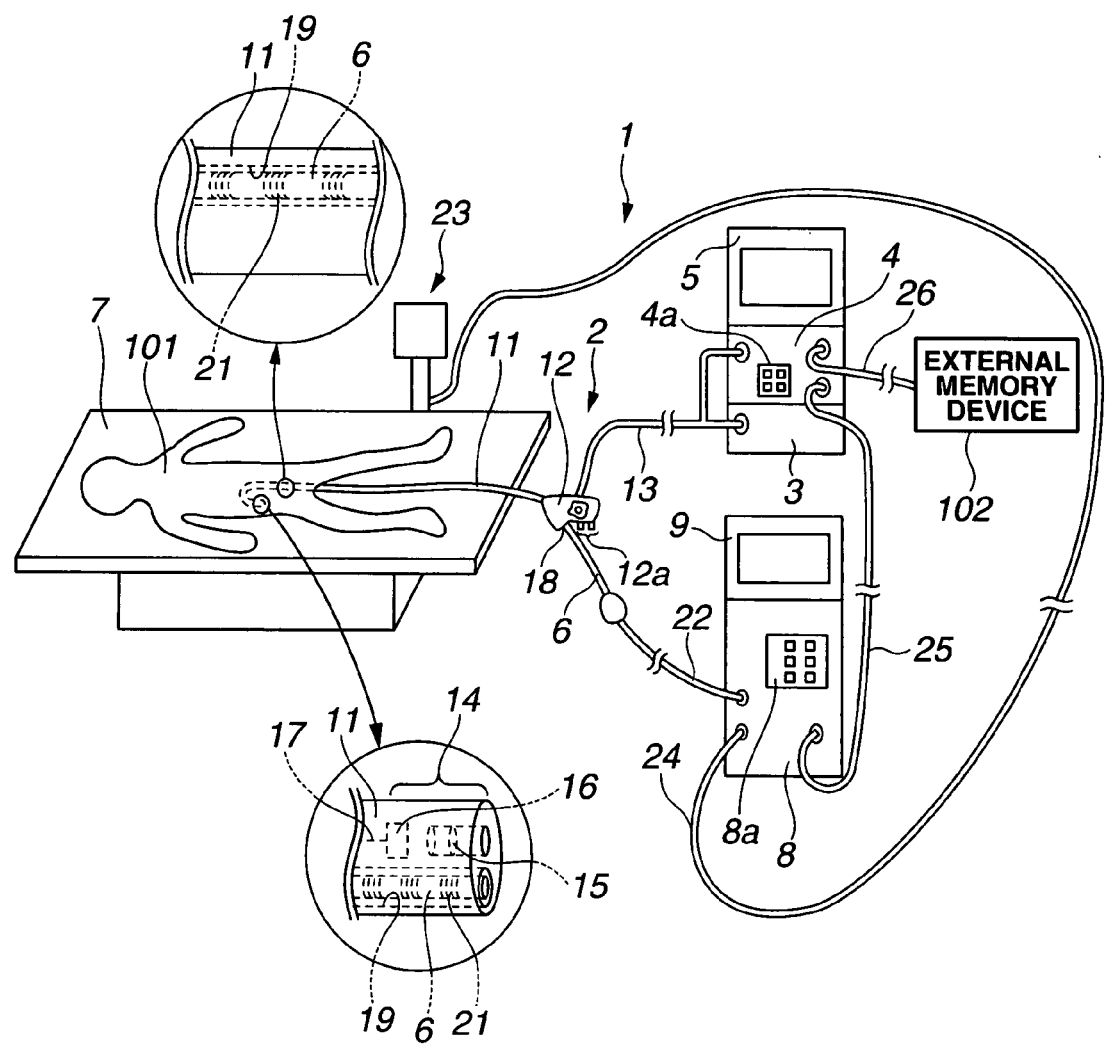
FIG. 1 is a diagram illustrating a configuration of an essential part of an endoscope system in which an endoscope insertion shape detecting device according to the present invention is used.
Figure 2:
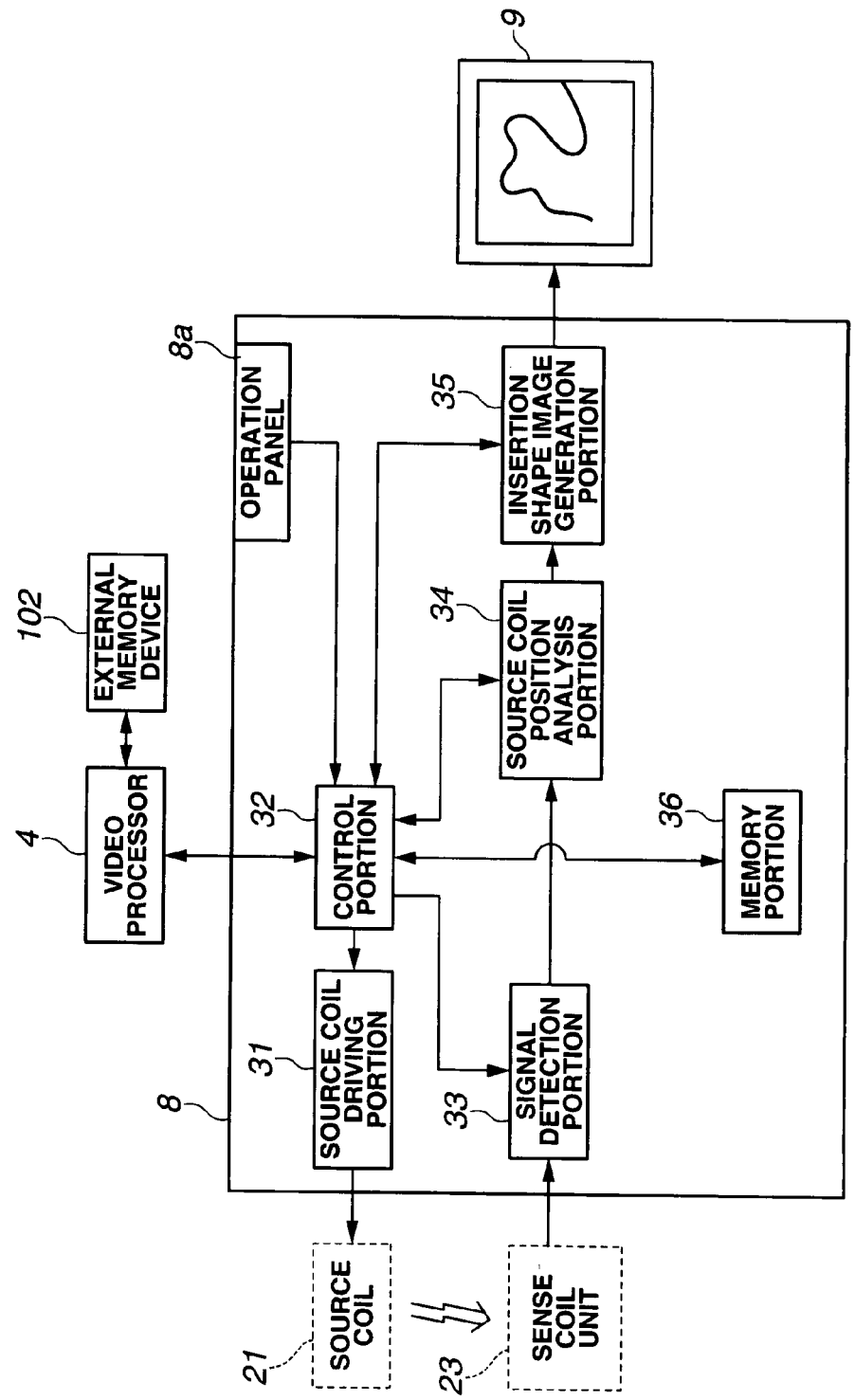
FIG. 2 is a block diagram illustrating an example of an internal configuration of the endoscope insertion shape detecting device in FIG. 1.
Figure 3:
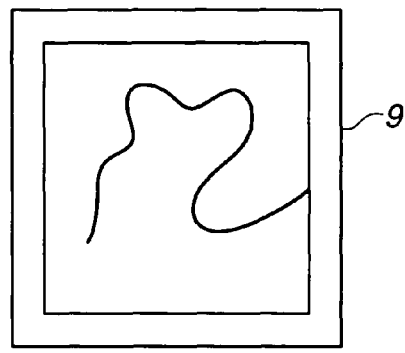
FIG. 3 is a view illustrating an example of an insertion shape figure of an endoscope insertion portion generated by the endoscope insertion shape detecting device in FIG. 1.
Figure 4:
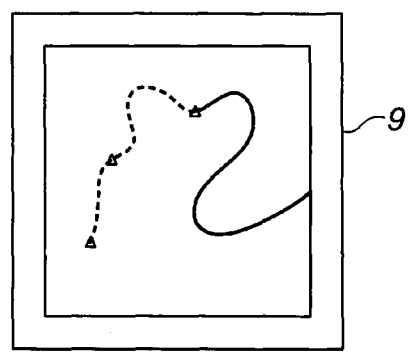
FIG. 4 is a view illustrating an example when a mark is generated along with the insertion shape figure in FIG. 3.
Figure 5:
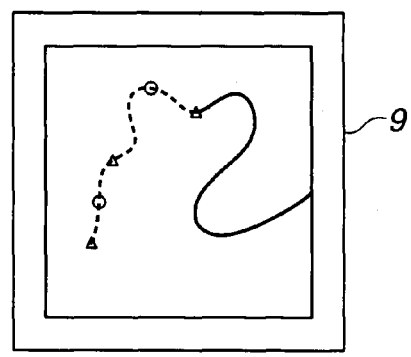
FIG. 5 is a view illustrating an example different from FIG. 4 when a mark is generated along with the insertion shape figure in FIG. 3.
Figure 6:
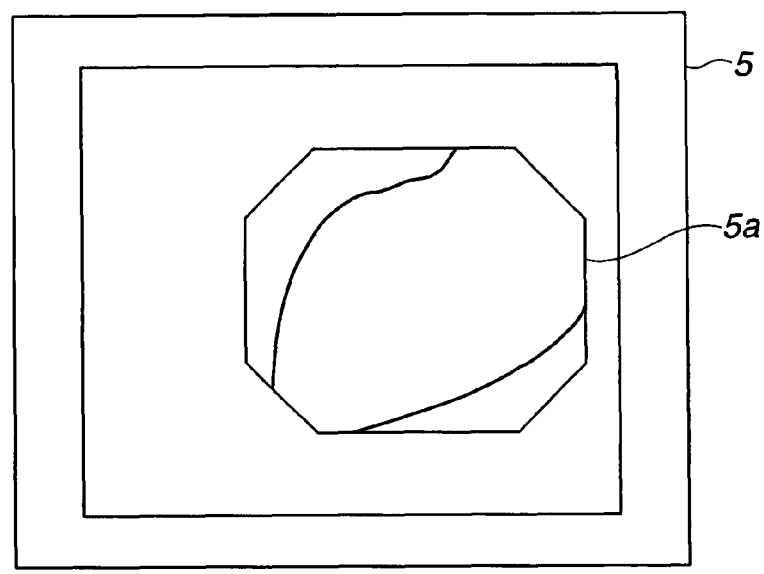
FIG. 6 is a view illustrating an example of an endoscopic image on the basis of an image of a photographic subject picked up by an endoscope in FIG. 1.
Figure 7:
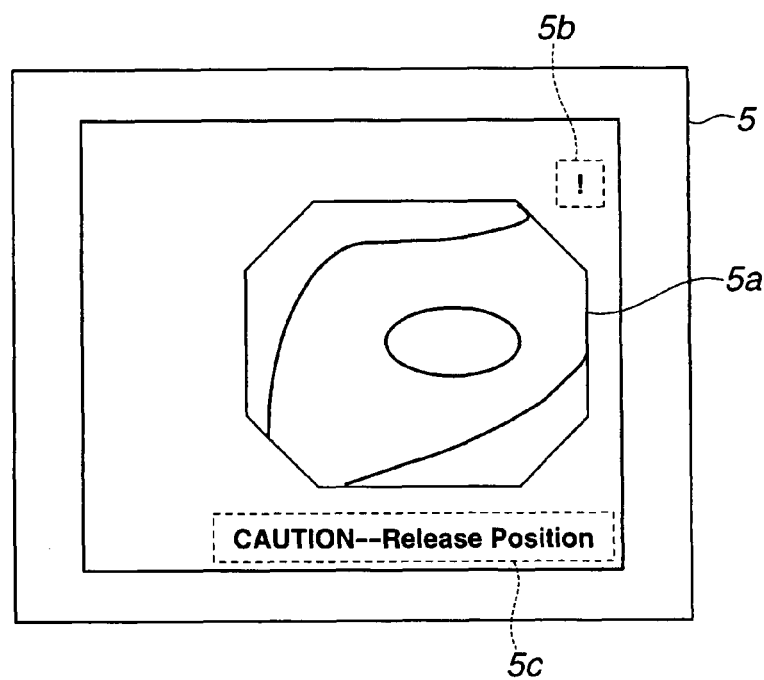
FIG. 7 is a view illustrating an example when notification information is displayed indicating that a location where a release instruction is made in the past observation is being reached along with an endoscopic image on the basis of a photographic subject picked up by an endoscope in FIG. 1.
Figure 8:
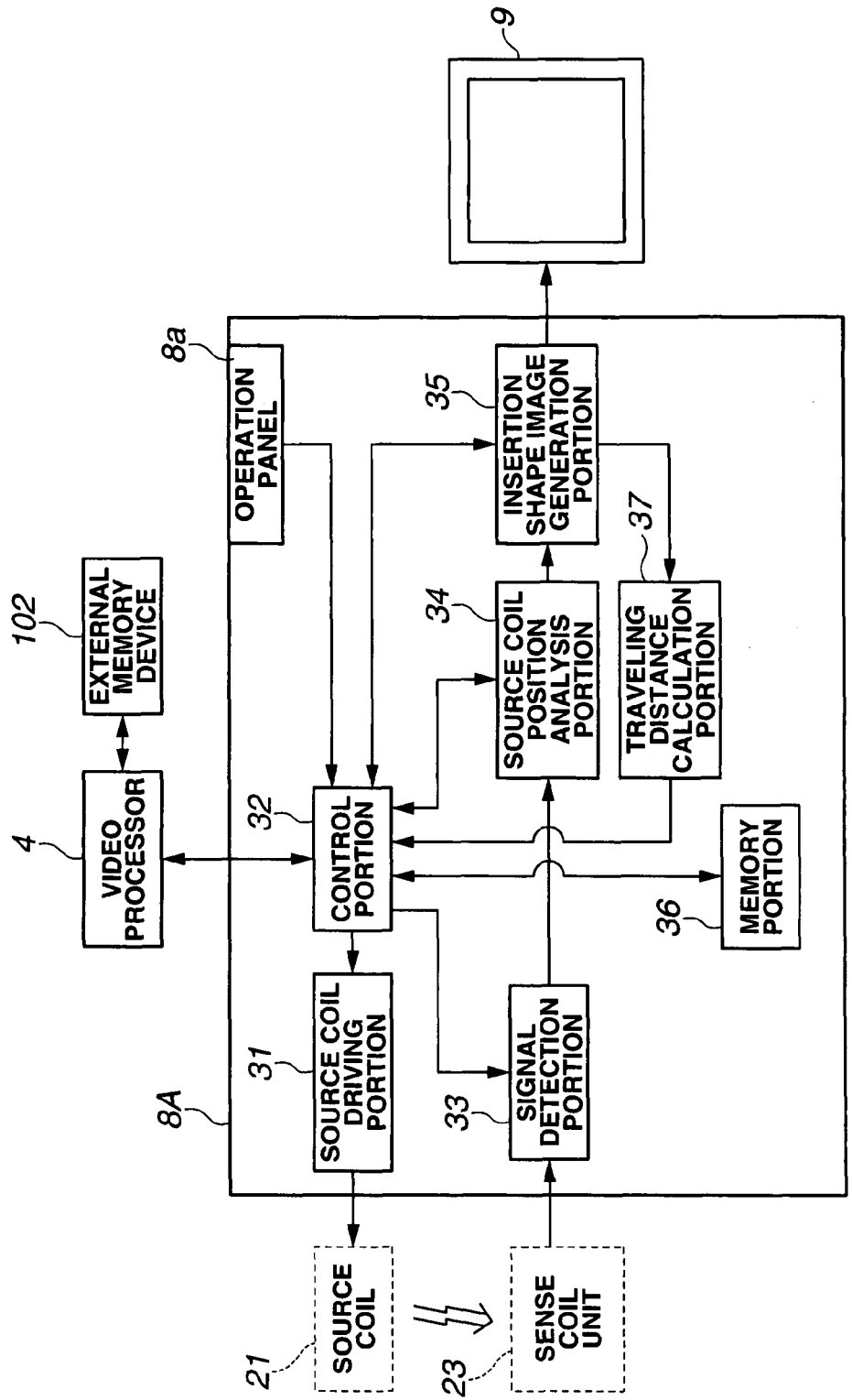
FIG. 8 is a block diagram illustrating an example different from FIG. 2 of an internal configuration of the endoscope insertion shape detecting device in FIG. 1.
Figure 9:
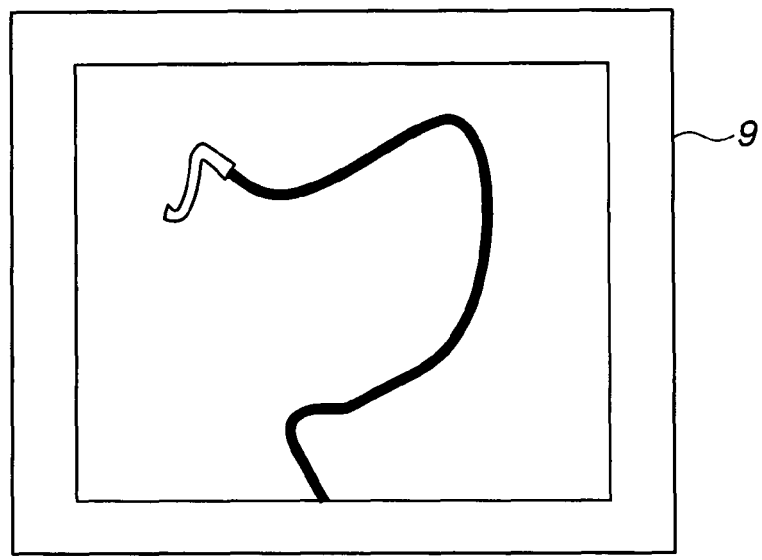
FIG. 9 is a view illustrating an example of an insertion shape figure of the endoscope insertion portion generated by the endoscope insertion shape detecting device in FIG. 8.
Figure 10:
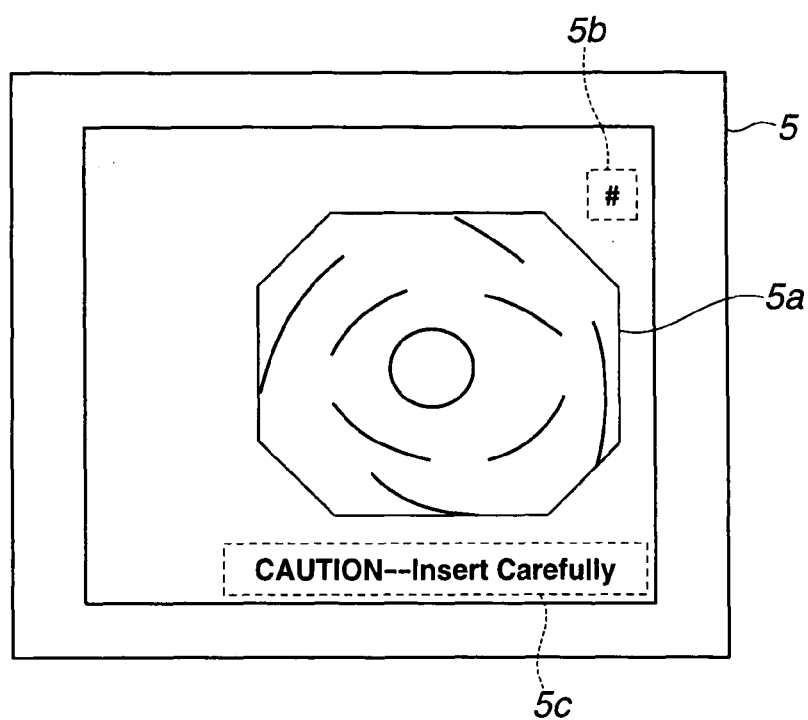
FIG. 10 is a view illustrating an example when notification information indicating that a spot requiring time for insertion is being reached or a spot where insertion requires time is approaching is displayed along with an endoscopic image on the basis of a photographic subject picked up by the endoscope in FIG. 1.

Embodiments of the present invention will be described referring to the attached drawings. FIGS. 1 to 13 relate to the embodiments of the present invention. FIG. 1 is a diagram illustrating a configuration of an essential part of an endoscope system in which an endoscope insertion shape detecting device according to the present invention is used. FIG. 2 is a block diagram illustrating an example of an internal configuration of the endoscope insertion shape detecting device in FIG. 1. FIG. 3 is a view illustrating an example of an insertion shape figure of an endoscope insertion portion generated by the endoscope insertion shape detecting device in FIG. 1. FIG. 4 is a view illustrating an example when a mark is generated along with the insertion shape figure in FIG. 3. FIG. 5 is a view illustrating an example different from FIG. 4 when a mark is generated along with the insertion shape figure in FIG. 3. FIG. 6 is a view illustrating an example of an endoscopic image on the basis of an image of a photographic subject picked up by an endoscope in FIG. 1. FIG. 7 is a view illustrating an example when notification information is displayed indicating that a spot where a release instruction is made in the past observation is being reached along with an endoscopic image on the basis of a photographic subject picked up by an endoscope in FIG. 1. FIG. 8 is a block diagram illustrating an example different from FIG. 2 of an internal configuration of the endoscope insertion shape detecting device in FIG. 1. FIG. 9 is a view illustrating an example of an insertion shape figure of the endoscope insertion portion generated by the endoscope insertion shape detecting device in FIG. 8. FIG. 10 is a view illustrating an example when notification information indicating that a spot requiring time for insertion is being reached or a location where insertion requires time is being approached is displayed along with an endoscopic image on the basis of a photographic subject picked up by the endoscope in FIG. 1.

Figure 11:
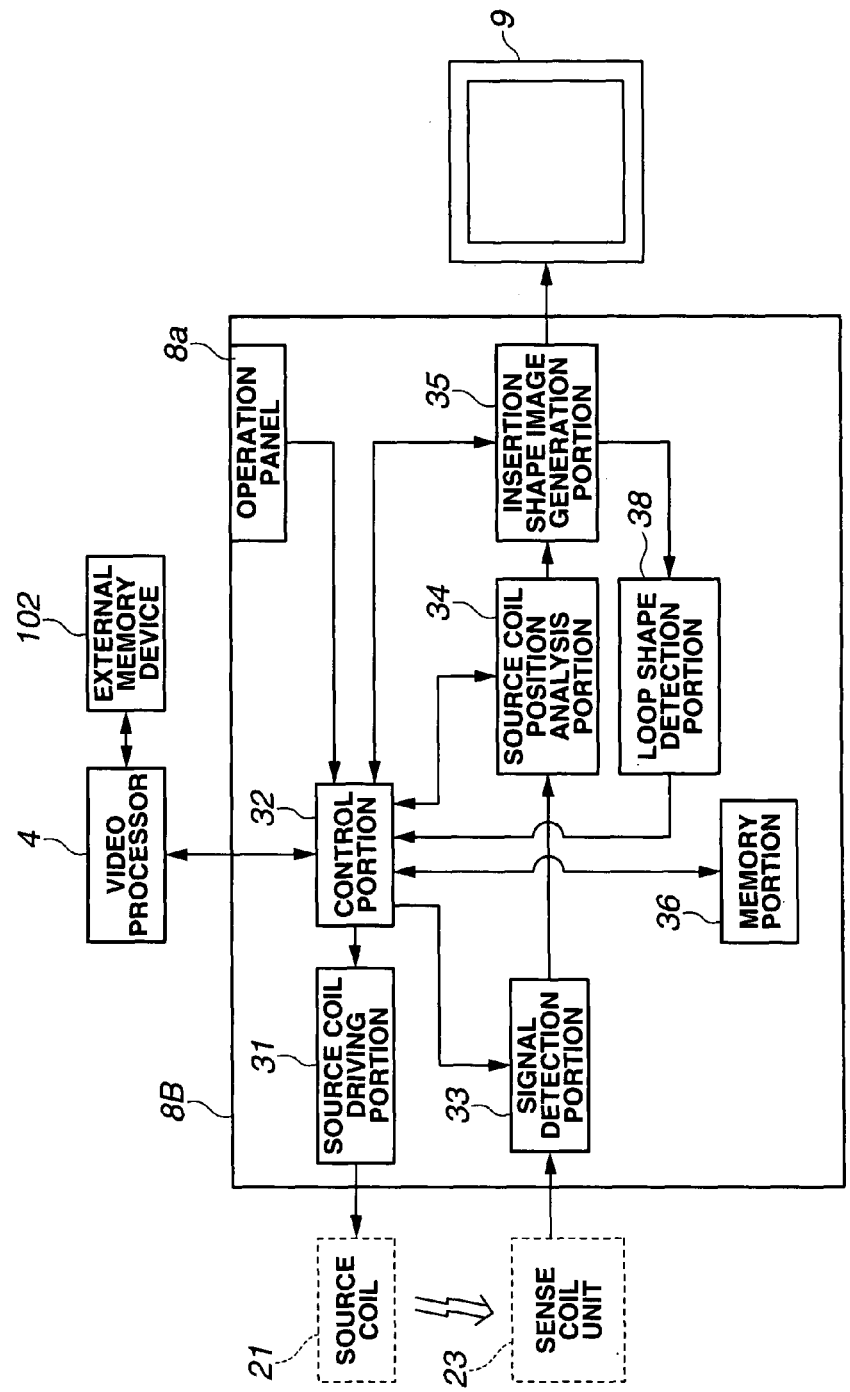
FIG. 11 is a block diagram illustrating an example different from FIG. 2 and FIG. 8 of the internal configuration of the endoscope insertion shape detecting device in FIG. 1.
Figure 12:
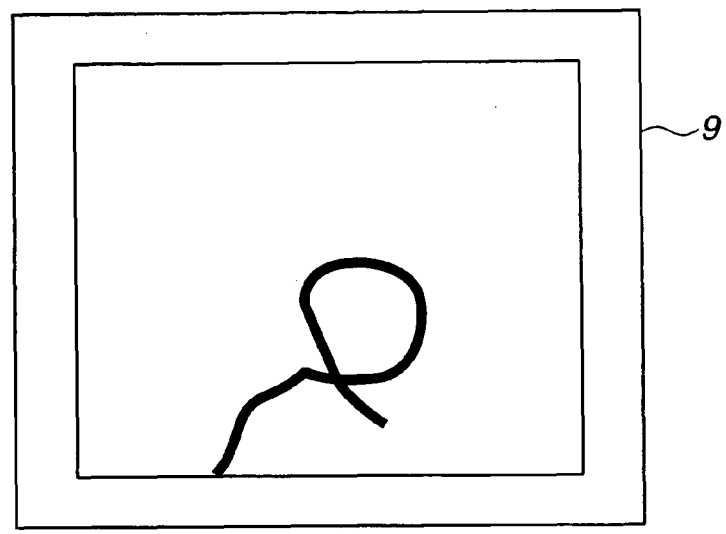
FIG. 12 is a view illustrating an example of an insertion shape figure of the endoscope insertion portion generated by the endoscope insertion shape detecting device in FIG. 11.
Figure 13:
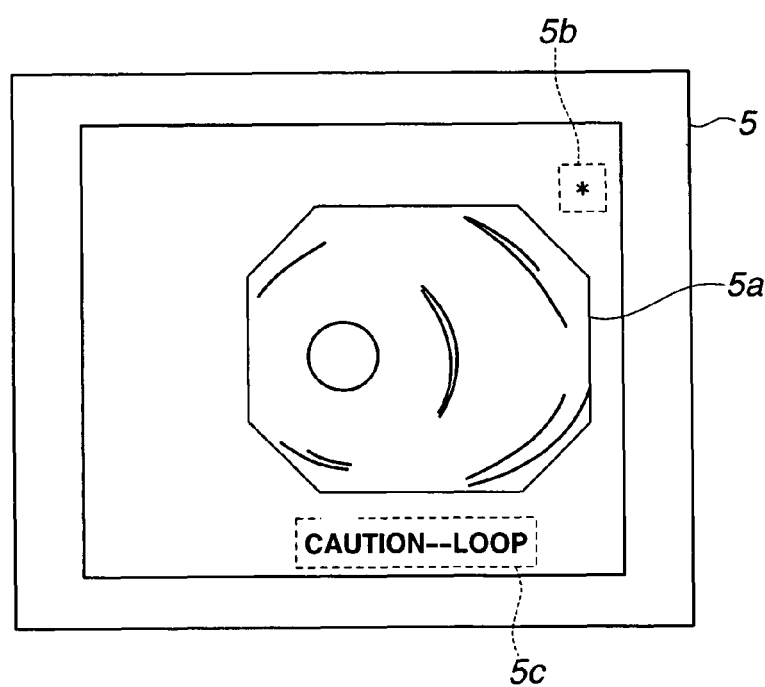
FIG. 13 is a view illustrating an example when notification information indicating that the endoscope insertion portion forms a loop shape or there is a possibility that the endoscope insertion portion forms a loop shape is displayed along with an endoscopic image on the basis of an image of a photographic subject pickup up by the endoscope in FIG. 1.

FIG. 11 is a block diagram illustrating an example different from FIG. 2 and FIG. 8 of the internal configuration of the endoscope insertion shape detecting device in FIG. 1. FIG. 12 is a view illustrating an example of an insertion shape figure of the endoscope insertion portion generated by the endoscope insertion shape detecting device in FIG. 11. FIG. 13 is a view illustrating an example when notification information indicating that the endoscope insertion portion has formed a loop shape or there is a possibility that the endoscope insertion portion forms a loop shape is displayed along with an endoscopic image on the basis of an image of a photographic subject pickup up by the endoscope in FIG. 1.

An endoscope system 1 comprises, as shown in FIG. 1, an endoscope 2 which picks up an image of a photographic subject existing within a body cavity of a patient 101 as a subject outputting the image of the picked up photographic subject as an image pickup signal, a light source device 3 for supplying illumination light for illuminating the photographic subject to be picked up by the endoscope 2, a video processor 4 for carrying out image processing and the like for the image pickup signal outputted from the endoscope 2 and outputting the signal as a video signal, a monitor 5 as a display portion for displaying an image of the photographic subject picked up by the endoscope 2 on the basis of the video signal outputted form the video processor 4, an insertion shape detection probe 6, a bed 7 on which the patient 101 can be loaded, an endoscope insertion shape detecting device 8, a monitor 9, and a sense coil unit 23.

The endoscope 2 comprises an endoscope insertion portion 11 having a dimension and a shape capable of insertion into a body cavity of the patient 101, an endoscope operation portion 12 continuously provided at the proximal end of the endoscope insertion portion 11, and a universal cord 13 having one end extended from the side of the endoscope operation portion 12 and the other end capable of being connected to the light source device 3 and the video processor 4.

Inside the endoscope distal end portion 14 provided at the distal end side of the endoscope insertion portion 11, an image pickup portion is provided having an objective optical system 15 for forming an image of a photographic subject and a CCD (solid image pickup device) 16 for picking up an image of the photographic subject formed by the objective optical system 15 and outputting the image of the picked up photographic subject as an image pickup signal are provided. An image pickup signal outputted from the CCD 16 is outputted to a signal line 17 with one end connected to the rear of the CCD 16. The signal line 17 is provided so as to be inserted through the endoscope insertion portion 11, the endoscope operation portion 12, and the universal cord 13, one end of which is connected to the rear of the CCD 16 and the other end is electrically connected to the video processor 4. By this configuration, the image pickup signal outputted from the CCD 16 is outputted to the video processor 4 via the signal line 17. A light guide, not shown, is inserted through the endoscope insertion portion 11, the endoscope operation portion 12, and the universal cord 13. By this configuration, the illumination light supplied from the light source device 3 is emitted to the photographic subject to be picked up by the CCD 16 through the light guide and an illumination lens, not shown, provided at the endoscope distal end portion 14.

On the side of the endoscope operation portion 12, a probe insertion port 18 for insertion of the insertion shape detection probe 6 is provided. The probe insertion port 18 communicates with a probe channel 19 provided to be inserted through the endoscope insertion portion 11 and is formed so that the insertion shape detection probe 6 can be inserted through the probe channel 19.

Also, on the side of the endoscope operation portion 12, a scope switch 12a is provided capable of operation instructions such as a freeze instruction for displaying a still image on the monitor 5, a release instruction for storing the still image in an external memory device 102 and the like.

The video processor 4 is provided with a front panel 4a on the exterior surface having one or more switches or the like capable of giving an operation instruction such as patient information setting instruction for setting information on the patient 101 such as an ID number (hereinafter abbreviated as patient information) as an operation instruction to the video processor 4 and the like.

The video processor 4 is connected to the endoscope insertion shape detecting device 8 via a cable 25 and also connected to the external memory device 102 via a cable 26.

Therefore, the video processor 4 can store information indicating position information of each source coil 21 provided at the insertion shape detection probe 6 outputted from the endoscope insertion shape detecting device 8 and information such as information indicating the insertion shape of the endoscope insertion portion 11, for example, in the external memory device 102 in association with the patient information as subject information and a still image at timing when the release instruction is given (hereinafter abbreviated as a release image). Also, the video processor 4 can output notification information according to the information outputted from the endoscope insertion shape detecting device 8 superimposed on a video signal generated by image processing to the monitor 5.

The video processor 4 detects an operation instruction made at the scope switch 12a and outputs the detection result to the endoscope insertion shape detecting device 8. Also, the video processor 4 outputs the patient information set by the operation instruction at the front panel 4a and the information on timing when the release instruction is made at the scope switch 12a to the endoscope insertion shape detecting device 8.

The insertion shape detection probe 6 has a dimension and a shape capable of being inserted into the probe insertion port 18 and the probe channel 19 of the endoscope 2, and a plurality of source coils 21 as a plurality of magnetic field generating elements for generating a magnetic field according to the insertion shape of the endoscope insertion portion 11 in the body cavity are provided having a predetermined interval between each of them. Also, a cable 22 to be connected to the endoscope insertion shape detecting device 8 is extended from the proximal end of the insertion shape detection probe 6. And the endoscope insertion shape detecting device 8 generates a magnetic field at each of the source coils 21 by driving each source coil 21 via the cable 22. Each of the plurality of source coils 21 is not limited to those provided separately from the endoscope insertion portion 11 but may be provided integrally inside the endoscope insertion portion 11.

The sense coil unit 23 as a magnetic field detection portion provided outside the endoscope insertion shape detecting device 8 as a part of the endoscope insertion shape detecting device is arranged at a position as shown in FIG. 1, for example, capable of detecting a magnetic field generated at each source coil 21 of the insertion shape detection probe 6 and outputs the detected magnetic field to the endoscope insertion shape detecting device 8 via a cable 24 as a magnetic field signal according to the intensity of the magnetic field.

The endoscope insertion shape detecting device 8 comprises an operation panel 8a having one or more switches or the like on the exterior surface capable of giving operation instructions such as observation end instruction for instructing that single observation has been completed and operation instructions for selecting and displaying desired information on the monitor 9 in the various information stored in the endoscope insertion shape detecting device 8, for example, as an operation instruction to the endoscope insertion shape detecting device 8 and the like.

Also, the endoscope insertion shape detecting device 8 has a source coil driving portion 31 for driving each source coil 21, a control portion 32 for controlling each part of the endoscope insertion shape detecting device 8, a signal detection portion 33, a source coil position analysis portion 34, an insertion shape image generation portion 35, and a memory portion 36 inside as shown in FIG. 2.

The signal detection portion 33 amplifies the magnetic field signal outputted from the sense coil unit 23 to a level capable of signal processing on the basis of control by the control portion 32 and outputs the amplified magnetic field signal to the source coil position analysis portion 34.

The source coil position analysis portion 34 as the insertion shape detection portion detects the insertion shape of the endoscope insertion portion 11 by estimating a three-dimensional position coordinate of each source coil 21 according to the magnetic signal outputted from the signal detection portion 33 on the basis of the control by the control portion 32. And the source coil position analysis portion 34 outputs the three-dimensional position coordinate of each source coil 21 and the detection result of the insertion shape of endoscope insertion portion 11 as the position information signal. Also, the source coil position analysis portion 34 can detect how far the endoscope insertion portion 11 having the insertion shape detection probe 6 inserted has been inserted into the body cavity of the patient 101 on the basis of the estimated three-dimensional position coordinate of each source coil 21.

The insertion shape image generation portion 35 calculates a three-dimensional shape of the endoscope insertion portion 11 according to the position information signal of each source coil 21 outputted from the source coil position analysis portion 34 on the basis of the control by the control portion 32. Also, the insertion shape image generation portion 35 generates the insertion shape figure of the endoscope insertion portion 11 from the three-dimensional shape and outputs the figure as an insertion shape figure signal. Thus, on the monitor 9, the insertion shape figure of the endoscope insertion portion 11 according to the insertion shape figure signal outputted from the insertion shape image generation portion 35 is displayed.

The control portion 32 comprised by a CPU and the like carries out control so that each source coil 21 generates a magnetic field at predetermined timing and with predetermined different frequencies by controlling the driving state of the source coil driving portion 31. Also, the control portion 32 outputs a timing signal for controlling the timing when each of the signal detection portion 33, the source coil position analysis portion 34 and the insertion shape image generation portion 35 executes processing to each portion. Moreover, the control portion 32 performs control of each portion provided at the endoscope insertion shape detecting device 8 on the basis of an operation instruction made at the operation panel 8a.

The control portion 32 as a marking processing portion executes control for the insertion shape image generation portion 35 for adding a mark indicating timing when a release instruction is made to the insertion shape figure for output at timing on the basis of release timing information outputted from the video processor 4. By this control, the insertion shape image generation portion 35 generates any one of figures including a circle, a triangle, a square, a star and the like as the mark, superimposes the mark on the insertion shape figure signal and outputs it to the monitor 9. Thus, on the monitor 9, the insertion shape figure of the endoscope insertion portion 11 is displayed with a spot where the release instruction is made in the currently conducted observation is marked. In the insertion shape figure of the endoscope insertion portion 11 of the present embodiment, the spot where a single mark is displayed shall substantially match coordinate where the distal end of the endoscope distal end portion 14 exists (on the screen of the monitor 9) when the release instruction is given at the scope switch 12a. Also, the insertion shape image generation portion 35 may superimpose numerals such as 1, 2, 3 ... sequentially added to the mark on the insertion shape figure signal according to the order that the release instruction is made in the currently conducted observation.

When the control portion 32 detects that an observation end instruction is given at the operation panel 8a, the control portion carries out processing of storing in the memory portion 36 the position information signal outputted from the source coil position analysis portion 34 and the insertion shape figure signal outputted from the insertion shape image generation portion 35, while associating them with the patient information outputted from the video processor 4, as first observation information in first observation.

The above-mentioned first observation information is outputted not only to the memory portion 36 but also to the video processor 4. Thus, the video processor 4 can store each of the information held by the first observation information outputted from the endoscope insertion shape detecting device 8 in the external memory device 102 in association with each release image obtained in the first observation.

In the above-mentioned processing, the first observation information outputted to the video processor 4 and the memory portion 36 includes the mark position information, which is the information on the display position of each mark (coordinate on the screen of the monitor 9) displayed on the monitor 9 in the state added to the insertion shape figure generated during the one observation as well as the insertion shape figure of the endoscope insertion portion 11 displayed on the monitor 9 during one observation. The mark position information is not limited to the display position of each mark displayed on the monitor 9 but may be information set on the basis of the length by which the endoscope insertion portion 11 is inserted into the body cavity of the patient 101.

As a result, in the memory portion 36, information associated with the patient information in one observation, the insertion shape figure of the endoscope insertion portion 11 in the one observation, and the mark position information in the one observation are stored as the first observation information.

When the control portion 32 refers to the first observation information stored in the memory portion 36 in the second observation carried out after the first observation and detects that the patient information in the first observation information matches the patient information outputted from the video processor 4 in the second observation, the control portion carries out control for the insertion shape image generation portion 35 for adding the first mark according to the first observation information and the second mark indicating the timing when the release instruction is made in the second observation to the insertion shape figure for output. By this control, the insertion shape image generation portion 35 generates figures different from each other in a circle, a triangle, a square, a star and the like as the first mark and the second mark and then, superimposes the first mark and the second mark on the insertion shape figure signal and outputs it to the monitor 9. Thus, on the monitor 9, together with the insertion shape figure of the endoscope insertion portion 11 in the second observation, the spot where the release instruction is made in the second observation is marked as the second mark and the spot where the release instruction is made in the first observation is also displayed in the state marked by the first mark.

The control portion 32 may perform control for the insertion shape image generation portion 35 for adding the first mark corresponding to the location to the insertion shape figure for output in the above-mentioned processing executed at the second observation, only when it is detected that the portion corresponding to the endoscope distal end portion 14 of the insertion shape figure of the endoscope insertion portion has approached the location where the release instruction was made in the first observation.

Also, when the control portion 32 as the position detection information output portion detects that the portion corresponding to the endoscope distal end portion 14 of the insertion shape figure of the endoscope insertion portion 11 generated in the second observation is overlapped with the first mark indicating the spot where the release instruction is made in the first observation (existing at the coordinate proximate to the first mark) on the basis of the insertion shape figure signal outputted from the insertion shape image generation portion 35, the control portion outputs the detection result as the already observed portion information to the video processor 4.

The video processor 4 generates notification information having at least one of the character strings, patterns, symbols, figures and the like indicating that the endoscope distal end portion 14 is reaching the spot where the release instruction is made in the first observation on the basis of the already observed portion information outputted from the endoscope insertion shape detecting device 8 and outputs the notification information superimposed on the video signal to the monitor 5. Thus, on the monitor 5, together with the image of the photographic subject picked up by the endoscope 2, the above-mentioned notification information is displayed as an image when the endoscope distal end portion 14 is reaching the spot where the release instruction is made in the first observation.

The video processor 4 may execute processing of sounding a sound for drawing attention of a user by a speaker, not shown, in accordance with the timing when the notification information as an image is displayed on the monitor 5.

Moreover, when the control portion 32 detects that the observation end instruction is made at the operation panel 8a and also detects that the patient information in the first observation information matches the patient information outputted from the video processor 4 in the second observation, the control portion executes processing of storing the position information signal outputted from the source coil position analysis portion 34 in the second observation and the insertion shape figure signal outputted from the insertion shape image generation portion 35 in the second observation in association with the patient information held by the first observation information in the memory portion 36 as additional information of the first observation information.

The additional information of the first observation information is outputted not only to the memory portion 36 but also to the video processor 4. Thus, the video processor 4 can store the information held by the additional information of the first observation information outputted from the endoscope insertion shape detecting device 8 in the external memory device 102 as the information added to the first observation information stored in advance in association with each release image obtained in the second observation.

Also, when the control portion 32 detects in the second observation conducted after the first observation that the patient information in the first observation information does not match the patient information outputted from the video processor 4 in the second observation by referring to the first observation information stored in the memory portion 36, the control portion executes control for the insertion shape image generation portion 35 for adding a mark indicating timing when the release instruction is made in the second observation for output. By this control, the insertion shape image generation portion 35 generates a figure such as a circle, a triangle, a square and the like as the mark and then, outputs the mark superimposed on the insertion shape figure signal to the monitor 9. Thus, on the monitor 9, together with the insertion shape figure of the endoscope insertion portion 11 in the second observation, the spot where the release instruction is made in the second observation is displayed in the marked state.

When the control portion 32 detects that the observation end instruction is made at the operation panel 8a and also detects that the patient information in the first observation information does not match the patient information outputted from the video processor 4 in the second observation, the control portion executes processing of storing the position information signal outputted from the source coil position analysis portion 34 in the second observation and the insertion shape figure signal outputted from the insertion shape image generation portion 35 in the memory portion 36 as the second observation information, that is, the observation information different from the first observation information.

The above-mentioned second observation information is outputted not only to the memory portion 36 but also to the video processor 4. Thus, the video processor 4 can store the information held by the second observation information outputted from the endoscope insertion shape detecting device 8 in the external memory device 102 as the observation information different from the first observation information in association with each release image obtained in the second observation.

Next, operation of the endoscope system 1 according to the present embodiment will be described.

First, a user inputs patient information as information relating to the patient 101 by operating the front panel 4a of the video processor 4. The patient information inputted by the user is held in the video processor 4 and also outputted to the endoscope insertion shape detecting device 8.

The control portion 32 of the endoscope insertion shape detecting device 8 detects whether there is observation information having the patient information in the observation information stored in the memory portion 36 (and the external memory device 102) on the basis of the patient information outputted from the video processor 4. When the control portion 32 detects that the observation information having the patient information is not stored in the memory portion 36 (or the external memory device 102, either), the control portion executes the following processing.

The user inputs the patient information and then, inserts the insertion shape detection probe 6 from the probe insertion port 18 into the endoscope 2. Moreover, the user inserts the endoscope insertion portion 11 into the body cavity of the patient 101 in the state where the universal cord 13, the cable 22, the cable 24, the cable 25 and the cable 26 are connected appropriately and each portion is powered on.

The CCD 16 picks up an image of a photographic subject illuminated by illumination light supplied from the light source device 3 and outputs the image of the picked up photographic subject as an image pickup signal. And the video processor 4 generates a video signal by applying image processing to the image pickup signal outputted from the CCD 16 and outputs the video signal to the monitor 5. The monitor 5 displays an image of the photographic subject picked up by the endoscope 2 on the basis of the video signal outputted from the video processor 4.

Also, the control portion 32 of the endoscope insertion shape detecting device 8 executes control so that each source coil 21 generates a magnetic field at predetermined timing and in predetermined different frequencies by controlling the driving state of the source coil driving portion 31. And each source coil 21 generates a magnetic field according to the insertion shape of the endoscope insertion portion 11 in the body cavity on the basis of the control contents of the control portion 32.

The sense coil unit 23 detects a magnetic field generated from each source coil 21 and outputs the detected magnetic field as a magnetic field signal corresponding to the intensity of the magnetic field to the endoscope insertion shape detecting device 8 via the cable 24.

The endoscope insertion shape detecting device 8 amplifies the inputted magnetic field signal and estimates a three-dimensional position coordinate of each source coil 21 according to the amplified magnetic field signal and generates and outputs the insertion shape figure of the endoscope insertion portion 11 on the basis of the three-dimensional coordinate of each source coil 21. Thus, when the endoscope insertion portion 11 is inserted to the deepest side in the body cavity of the patient 101, the insertion shape figure of the endoscope insertion portion 11 is displayed on the monitor 9 by a solid line as shown in FIG. 3, for example.

And the user inserts the endoscope insertion portion 11 into the deepest side in the body cavity of the patient 101 and then, makes observation of a desired portion while removing the inserted endoscope insertion portion 11.

When the control portion 32 detects that an operation to remove the endoscope insertion portion 11 has been performed on the basis of the position information signal outputted from the source coil position analysis portion 34, the control portion carries out control for the insertion shape image generation portion 35 so that the portion corresponding to the length of removal is drawn by a broken line, for example, in the insertion shape figure of the endoscope insertion portion 11 drawn by the solid line. Thus, when the endoscope insertion portion 11 is being removed from the body cavity of the patient 101, the portion remaining in the body cavity is displayed by the solid line on the monitor as shown in FIG. 4, for example, and the portion having been removed from the body cavity is displayed by the broken line on the monitor 9.

After that, the user observes a desired portion and in order to store the state of the photographic subject at the desired portion as a still image, the user gives a release instruction by operating the scope switch 12a.

When the video processor 4 detects that the release instruction was made at the scope switch 12a, the video processor generates a release image according to the image of the photographic subject at the desired portion and stores the release image in the external memory device 102 in association with the patient information of the patient 101.

Also, the control portion 32 carries out control for the insertion shape image generation portion 35 of adding a mark indicating timing when the release instruction is made to the insertion shape figure for output at timing on the basis of the release timing information outputted from the video processor 4. Thus, a spot where the release instruction is made is displayed on the monitor 9 in the state marked as a triangle, for example.

After that, when the control portion 32 detects that the observation end instruction is made at the operation panel 8a, the control portion carries out control for storing the position information signal outputted from the source coil position analysis portion 34 and the insertion shape figure signal outputted from the insertion shape image generation portion 35 in association with the patient information outputted from the video processor 4 in the memory portion 36 as the first observation information in the first observation.

Also, the video processor 4 detects a release image associated with the patient information held in the first observation information among the release images stored in the external memory device 102, that is, each release image obtained in the first observation on the basis of the first observation information outputted from the endoscope insertion shape detecting device 8. And the video processor 4 stores the first observation information in the external memory device 102 in association with each release image obtained in the first observation.

After the first observation, the user makes the second observation using the endoscope system 1 for the patient 101 in order to check the course and the like of the treatment conducted at the first observation.

In this case, the user inputs the patient information similar to that inputted in the first observation by operating the front panel 4a of the video processor 4. The patient information inputted by the user is held at the video processor 4 and also outputted to the endoscope insertion shape detecting device 8.

The control portion 32 of the endoscope insertion shape detecting device 8 detects if there is observation information having the patient information in the observation information stored in the memory portion 36 (and the external memory device 102) on the basis of the patient information outputted from the video processor 4. When the control portion 32 detects that the observation information having the patient information is stored in the memory portion 36 (or at least one of the memory portion 36 and the external memory device 102), the control portion carries out the processing described below.

When the control portion 32 detects that the patient information in the first observation information matches the patient information outputted from the video processor 4 in the second observation for the patient 101 carried out after the first observation, the control portion carries out control for the insertion shape image generation portion 35 of adding a first mark according to the first observation information and a second mark indicating the timing when the release instruction is made in the second observation to the insertion shape figure for output. By this control, the insertion shape image generation portion 35 generates figures different from each other of a circle, a triangle, a square, a star and the like as the first mark and the second mark, superimposes the first mark and the second mark on the insertion shape figure signal and outputs it to the monitor 9. Thus, together with the insertion shape figure of the endoscope insertion portion 11 in the second observation, the spot where the release instruction is made in the second observation is marked as a circle and the spot where the release instruction is made in the first observation is marked as a triangle and displayed on the monitor 9 as shown in FIG. 5, for example.

Also, when the control portion 32 detects that the portion corresponding to the endoscope distal end portion 14 of the insertion shape figure of the endoscope insertion portion 11 generated in the second observation is overlapped with the first mark indicating the spot where the release instruction is made in the first observation as shown in FIG. 5, for example, on the basis of the insertion shape figure signal outputted from the insertion shape image generation portion 35, the control portion outputs the detection result to the video processor 4 as the already observed portion information.

And the video processor 4 generates notification information having at least any one of character strings, patterns, figures or the like indicating that the endoscope distal end portion 14 is reaching the spot where the release instruction is given in the first observation on the basis of the already observed portion information outputted from the endoscope insertion shape detecting device 8 and superimposes the notification information on the video signal and outputs it to the monitor 5.

In a state where the already observed portion information is not outputted from the endoscope insertion shape detecting device 8, the monitor 5 displays an image of the photographic subject inside the body cavity of the patient 101 as an endoscopic image 5a as shown in FIG. 6, for example. After that, when the endoscope insertion portion 11 is operated by the user and the already observed portion information is outputted from the endoscope insertion shape detecting device 8, the above-mentioned processing of superimposing the notification information on the video signal for output is carried out at the video processor 4. Thus, the monitor 5 displays a notification symbol 5b such as "!" and a notification message 5c such as "CAUTION—Release Position" as shown in FIG. 7 as notification information indicating that the endoscope distal end portion 14 is reaching the spot where the release instruction is made in the first observation together with the endoscopic image 5a.

The both above-mentioned notification symbol 5b and the notification message 5c are not limited to a case where both of them are displayed on the monitor 5 but at least either one may be displayed. Also, the above-mentioned notification symbol 5b and the notification message 5c may be such that a sound to draw attention of a user is sounded from a speaker, not shown, according to the timing when each of them is displayed on the monitor 5.

When the control portion 32 of the endoscope insertion shape detecting device 8 detects that one of the marks is selected by operation of the operation panel 8a, for example, when the insertion shape figure of the endoscope insertion portion 11 and the marks held by one observation information are displayed on the monitor 9, the control portion may carry out control for the video processor 4 so that the release image according to the detection result is read from the external memory device 102 and displayed on the monitor 5.

Also, the endoscope insertion shape detecting device 8 of the present embodiment can also display the insertion shape figure of the endoscope insertion portion 11 and the marks held in the desired observation information selected by operation by the user of the operation panel 8a among observation information obtained in the past observations stored in the memory portion 36 on the monitor 9.

Moreover, the video processor 4 in the present embodiment is not limited to that for storing a still image when a release instruction is made as a release image in the external memory device 102 in association with the patient information but may extract a peculiar still image picked up with a bleeding portion, a polyp or the like as a photographic subject and store the extracted peculiar still image in the external memory device 102 as a release image in association with the patient information, for example, when an image processing for an inputted image pickup signal is carried out.

As mentioned above, the endoscope insertion shape detecting device 8 of the present embodiment can output the information relating to the position where the release image is obtained, the information obtained in past observations for a predetermined patient, along with the information obtained in the currently conducted observation. By this, the endoscope insertion shape detecting device 8 of the present embodiment can show the position of each portion substantially accurately when a portion where a release image was obtained in the past in the observation of a body cavity of a predetermined patient such as a treatment portion and finding of a lesion is to be observed again, for example. As a result, the endoscope insertion shape detecting device 8 of the present embodiment can reduce a burden on a user when observation by an endoscope is carried out for a plurality of times for a predetermined patient.

In the present embodiment, the notification information displayed on the monitor 5 is not limited to the one indicating that the endoscope distal end portion 14 is reaching the spot where the release instruction is made in the past observations but may indicate that the endoscope distal end portion 14 is reaching a difficult insertion spot such as a spot requiring time for insertion of the endoscope insertion portion 11, a spot where a loop is formed when the endoscope insertion portion 11 is inserted or the like.

As a configuration of the endoscope insertion shape detecting device which can indicate that a spot where insertion of the endoscope insertion portion 11 is difficult is being reached as the notification information, an endoscope insertion shape detecting device 8A as shown in FIG. 8, for example, can be considered.

The endoscope insertion shape detecting device 8A shown in FIG. 8 further comprises a traveling distance calculation portion 37 in addition to the configuration of the endoscope insertion shape detecting device 8 shown in FIG. 2. Portions provided in the endoscope insertion shape detecting device 8A other than the traveling distance calculation portion 37 have substantially the same operation as that of the above-mentioned endoscope insertion shape detecting device 8 unless otherwise described.

The traveling distance calculation portion 37 detects a three-dimensional position coordinate of one coil provided at the most distal end of the insertion shape detection probe 6 in the source coils 21 per predetermined period, for example, on the basis of the position information signal outputted from the source coil position analysis portion 34, calculates a distance by which the one coil has moved in the predetermined period and outputs the calculation result to the control portion 32 as the traveling distance information.

When the control portion 32 detects that the traveling distance of one coil provided at the most distal end of the insertion shape detection probe 6 is not more than a predetermined threshold value within the predetermined period on the basis of the traveling distance information outputted from the traveling distance calculation portion 37, the control portion carries out control for the insertion shape image generation portion 35 that a color of a portion corresponding to the predetermined period in the insertion shape figure of the endoscope insertion portion 11 is changed for output or that the portion corresponding to the predetermined period is highlighted more than the other portions for output, for example.

The insertion shape image generation portion 35 outputs the insertion shape figure in the state where the portion corresponding to the predetermined period is highlighted in the insertion shape figure of the endoscope insertion portion 11 to the monitor 9 as an insertion shape figure signal as shown in FIG. 9, for example, on the basis of the control of the control portion 32. And the insertion shape figure signal is stored by the control portion 32 in the memory portion 36 as information in one observation information in association with the patient information outputted from the video processor 4. Thus, the endoscope insertion shape detecting device 8A can display the insertion shape figure in the highlighted manner on the monitor 9 in the state where the difficult insertion spot requiring time for insertion of the endoscope insertion portion 11 held by the desired observation information selected by operation of a user of the operation panel 8a is highlighted among the observation information obtained in the past observations and stored in the memory portion 36.

Also, when the control portion 32 detects that the traveling distance of one coil provided at the most distal end of the insertion shape detection probe 6 is not more than a predetermined threshold value in the predetermined period on the basis of the traveling distance information outputted from the traveling distance calculation portion 37, the control portion outputs difficult insertion portion information indicating that the one coil is reaching the difficult insertion spot to the video processor 4.

The video processor 4 generates notification information having at least one of character strings, patterns, figures and the like indicating that the endoscope distal end portion 14 is reaching the difficult insertion spot on the basis of the difficult insertion portion information outputted from the endoscope insertion shape detecting device 8 and superimposes the notification information on the video signal for output. Thus, the monitor 5 displays the notification symbol 5b such as "#" and the notification message 5c such as "CAUTION—Insert Carefully" as shown in FIG. 10, for example, along with the endoscopic image 5a.

As mentioned above, the endoscope insertion shape detecting device 8A has an effect that a user can easily recognize a spot where insertion of the endoscope insertion portion 11 requires time in addition to the above-mentioned effect of the endoscope insertion shape detecting device 8.

Also, the control portion 32 of the endoscope insertion shape detecting device 8A extracts one observation information, which is observation information having the patient information and including the insertion shape figure in the state where the difficult insertion spot is highlighted among the observation information obtained in the past observation stored in the memory portion 36 on the basis of the patient information outputted from the video processor 4 in the currently conducted observation. And when the one observation information can be extracted, the control portion 32 compares the insertion shape figure held by the one observation information with the insertion shape figure outputted from the insertion shape image generation portion 35 and determines if the endoscope distal end portion 14 has approached the difficult insertion spot in the currently conducted observation. Moreover, when the control portion 32 detects that the endoscope distal end portion 14 has approached the difficult insertion spot in the currently conducted observation, not relying on the determination result on the basis of the traveling distance information outputted from the traveling distance calculation portion 37, that is, before the one coil provided at the most distal end of the insertion shape detection probe 6 reaches the difficult insertion spot, the control portion outputs the difficult insertion portion information to the video processor 4.

The video processor 4 generates notification information having at least one of character strings, patterns, figures and the like indicating that the endoscope distal end portion 14 approaches the difficult insertion spot on the basis of the difficult insertion portion information outputted from the endoscope insertion shape detecting device 8 and superimposes the notification information on the video signal for output. Thus, the monitor 5 displays the notification symbol 5b such as "#" and the notification message 5c such as "CAUTION—Insert Carefully" as shown in FIG. 10, for example, as the notification information indicating that the endoscope distal end portion 14 has approached the difficult insertion spot along with the endoscopic image 5a.

As mentioned above, the endoscope insertion shape detecting device 8A has an effect that a user can easily recognize that the endoscope distal end portion 14 has approached the portion detected as the difficult insertion spot in the past in the currently conducted observation in addition to the above-mentioned effect.

Also, as a configuration of the endoscope insertion shape detecting device which can indicate the approach to the spot where insertion of the endoscope insertion portion 11 is difficult as the notification information, an endoscope insertion shape detecting device 8B as shown in FIG. 11 can be considered.

The endoscope insertion shape detecting device 8B shown in FIG. 11 further comprises a loop-shape detection device 38 in addition to the configuration of the endoscope insertion shape detecting device 8 shown in FIG. 2. Portions provided in the endoscope insertion shape detecting device 8B other than the loop-shape detection device 38 have substantially the same operation as that of the above-mentioned endoscope insertion shape detecting device 8 unless otherwise described.

When the loop-shape detection portion 38 detects at least one or more crossing spots shown as overlapping coordinates in the insertion shape figure of the endoscope insertion portion 11, for example, on the basis of the insertion shape figure signal outputted from the insertion shape image generation portion 35, the detection portion determines that a loop is formed by the endoscope insertion portion 11 in the body cavity of the patient 101 and outputs a loop-shape detection signal to the control portion 32 on the basis of the determination result. The loop-shape detection portion 38 may determine that the endoscope insertion portion 11 forms a loop shape in the body cavity of the patient 101 when there is at least one or more overlapping coordinates in the insertion shape figure of the endoscope insertion portion 11 and a blood pressure measured by a blood pressure meter, not shown, or a heart rate reaches a predetermined value or above.

The control portion 32 detects that the endoscope insertion forms a loop shape in the body cavity on the basis of the loop-shape detection signal outputted from the loop-shape detection portion 38 and stores the insertion shape figure of the endoscope insertion portion 11 as shown in FIG. 12, for example, generated by the insertion shape image generation portion 35 at the detection timing in the memory portion 36 in association with the patient information outputted from the video processor 4. Thus, the endoscope insertion shape detecting device 8B can display the insertion shape figure on the monitor 9 in the state where the endoscope insertion portion 11 forms a loop in the body cavity of the patient 101 held by the desired observation information selected by operation of the operation panel 8a performed by the user among the observation information obtained in the past observation stored in the memory portion 36.

The control portion 32 may store the blood pressure measured by a blood pressure meter, not shown, or heart rate at the timing when the loop-shape detection signal outputted from the loop-shape detection portion 38 in association with the insertion shape figure of the endoscope insertion portion 11 and the patient information outputted from the video processor 4 in the memory portion 36.

Moreover, the control portion 32 detects that the endoscope insertion portion 11 forms a loop shape in the body cavity on the basis of the loop-shape detection signal outputted from the loop-shape detection portion 38 and outputs the detection result as the loop-shape generation portion information to the video processor 4.

The video processor 4 generates notification information having at least one of character strings, patterns, figures and the like indicating that the endoscope insertion portion 11 forms a loop shape on the basis of the loop-shape generation portion information outputted from the endoscope insertion shape detecting device 8 and superimpose the notification information on the video signal for output. Thus, the monitor 5 displays the notification symbol 5b such as "*" and the notification message 5c such as "CAUTION—Loop" as shown in FIG. 13, for example, as notification information indicating that the endoscope insertion portion 11 forms a loop shape along with the endoscopic image 5a.

As mentioned above, the endoscope insertion shape detecting device 8B has an effect that the user can easily recognize where the endoscope insertion portion 11 forms a loop shape in addition to the above-mentioned effect of the endoscope insertion shape detecting device 8.

Also, the control portion 32 of the endoscope insertion shape detecting device 8B extracts one observation information, which is the observation information including the insertion shape figure having the patient information and in the state where a loop is formed among observation information obtained in the past observations stored in the memory portion 36 on the basis of the patient information outputted from the video processor 4 in the currently conducted observation. And when the control portion 32 can extract the one observation information, the control portion compares the insertion shape figure held by the one observation information with the insertion shape figure outputted from the insertion shape image generation portion 35 and determines if the endoscope distal end portion 14 has passed the coordinate corresponding to the crossing spot in the currently conducted observation. Moreover, when the control portion 32 detects that the endoscope distal end portion 14 has passed the crossing spot in the currently conducted observation on the basis of the determination result, not relying on the detection result on the basis of the loop-shape detection signal outputted from the loop-shape detection portion 38, that is, before the endoscope insertion portion 11 forms a loop shape in the body cavity, the control portion outputs the loop-shape generation portion information to the video processor 4.

The video processor 4 generates notification information having at least one of character strings, patterns, figures and the like indicating a possibility that the endoscope insertion portion 11 forms a loop shape on the basis of the loop-shape generation portion information outputted from the endoscope insertion shape detecting device 8 and superimpose the notification information on the video signal for output. Thus, as the notification information indicating a possibility that the endoscope insertion portion 11 forms a loop shape, the notification symbol 5b such as "*" and the notification message 5c such as "CAUTION—Loop" as shown in FIG. 13, for example, are displayed on the monitor 5 along with the endoscopic image 5a.

As mentioned above, the endoscope insertion shape detecting device 8B has an effect that the user can easily recognize that the endoscope distal end portion 14 has approached a portion where the endoscope insertion portion 11 formed a loop shape in the past in the currently conducted observation in addition to the above-mentioned effect.

The endoscope insertion shape detecting device 8A may further comprise the loop-shape detection portion 38 having the above-mentioned operation. Also, the endoscope insertion shape detecting device 8B may further comprise the traveling distance calculation portion 37 having the above-mentioned operation.

It is needless to say that the present invention is not limited to the above embodiments but various changes and application are possible within a range not departing from the gist of the invention.

What is claimed is:

1. An endoscope insertion shape detecting device comprising:
    an insertion shape detection portion for detecting an insertion shape of an endoscope insertion portion provided with an image pickup portion at the distal end, which can pick up an image of a photographic subject existing inside a subject;
    an insertion shape image generation portion for generating an insertion shape figure of the endoscope insertion portion according to the insertion shape;
    a marking processing portion for carrying out a control to add a mark to a portion corresponding to the distal end of the insertion shape figure for output as a control for the insertion shape image generation portion when an instruction to obtain a still image according to the image of the photographic subject is detected in a first observation for the subject, wherein during the first observation, the insertion shape detection portion detects the shape of the endoscope insertion portion in a body cavity portion;

a memory portion for storing information associated with subject information, which is information relating to the subject, the insertion shape figure, mark position information, which is information of a position to which the mark is added in the insertion shape figure in the first observation; and a position detection information output portion, the position detection information output portion comparing the position of the endoscope insertion portion in a second observation with the same subject with the position of the endoscope insertion portion in the first observation, and outputting position detection information indicating that the distal end portion in the second observation is reaching the location where the instruction is made in the first observation when the position detection information output portion detects during the second observation that information of the body cavity portion where time was required because of a difficulty for insertion of the endoscope insertion portion during the first observation stored in the memory portion, the position detection information output portion outputs position detection information indicating that the distal end portion is reaching the body cavity portion.

2. The endoscope insertion shape detecting device according to claim 1, further comprising a magnetic field detection portion for detecting a magnetic field emitted by a plurality of magnetic-field generation elements arranged at the endoscope insertion portion and outputting a magnetic field signal corresponding to the intensity of the magnetic field, wherein the insertion shape detection portion estimates a position of each magnetic-field generation element on a basis of the magnetic field signal outputted from the magnetic field detection portion and detects the insertion shape of the endoscope insertion portion on a basis of the estimation result.

3. The endoscope insertion shape detecting device according to claim 1, wherein the position detection information output portion stores, in the memory portion, information on a spot where a distance that the distal end portion of the endoscope insertion portion has moved in a predetermined period is not more than a predetermined threshold value during the first observation, as the information of the body cavity portion where time was required because of a difficulty for insertion of the endoscope insertion portion during the first observation.

4. The endoscope insertion shape detecting device according to claim 1, wherein when the position detection information output portion detects that information of a body cavity portion where the endoscope insertion portion forms a loop shape is stored in the memory portion in the second observation, the position detection information output portion outputs position detection information indicating that the distal end portion is reaching the body cavity portion.

5. The endoscope insertion shape detecting device according to claim 1, wherein the position detection information output portion confirms in the second observation that the subject to be a target of the second observation is the same as the subject to be the target of the first observation by referring to the subject information stored in the memory portion.

6. The endoscope insertion shape detecting device according to claim 2, wherein the position detection information output portion confirms in the second observation that the subject to be a target of the second observation is the same as the subject to be the target of the first observation by referring to the subject information stored in the memory portion.

7. The endoscope insertion shape detecting device according to claim 3, wherein the position detection information output portion confirms in the second observation that the subject to be a target of the second observation is the same as the subject to be the target of the first observation by referring to the subject information stored in the memory portion.

8. The endoscope insertion shape detecting device according to claim 4, wherein the position detection information output portion confirms in the second observation that the subject to be a target of the second observation is the same as the subject to be the target of the first observation by referring to the subject information stored in the memory portion.

9. The endoscope insertion shape detecting device according to claim 1, wherein the position detection information is displayed as predetermined notification information in a display portion on which an endoscopic image is displayed on a basis of the image of the photographic subject.

10. The endoscope insertion shape detecting device according to claim 2, wherein the position detection information is displayed as predetermined notification information in a display portion on which an endoscopic image is displayed on a basis of the image of the photographic subject.

11. The endoscope insertion shape detecting device according to claim 3, wherein the position detection information is displayed as predetermined notification information in a display portion on which an endoscopic image is displayed on a basis of the image of the photographic subject.

12. The endoscope insertion shape detecting device according to claim 4, wherein the position detection information is displayed as predetermined notification information in a display portion on which an endoscopic image is displayed on a basis of the image of the photographic subject.

13. The endoscope insertion shape detecting device according to claim 5, wherein the position detection information is displayed as predetermined notification information in a display portion on which an endoscopic image is displayed on a basis of the image of the photographic subject.

14. The endoscope insertion shape detecting device according to claim 6, wherein the position detection information is displayed as predetermined notification information in a display portion on which an endoscopic image is displayed on a basis of the image of the photographic subject.

15. The endoscope insertion shape detecting device according to claim 7, wherein the position detection information is displayed as predetermined notification information in a display portion on which an endoscopic image is displayed on a basis of the image of the photographic subject.

16. The endoscope insertion shape detecting device according to claim 8, wherein the position detection information is displayed as predetermined notification information in a display portion on which an endoscopic image is displayed on a basis of the image of the photographic subject.

17. The endoscope insertion shape detecting device according to claim 9, wherein
the predetermined notification information is information having at least one of symbols and messages.

18. The endoscope insertion shape detecting device according to claim 10, wherein
the predetermined notification information is information having at least one of symbols and messages.

19. The endoscope insertion shape detecting device according to claim 11, wherein
the predetermined notification information is information having at least one of symbols and messages.

20. The endoscope insertion shape detecting device according to claim 12, wherein
the predetermined notification information is information having at least one of symbols and messages.

21. The endoscope insertion shape detecting device according to claim 13, wherein
the predetermined notification information is information having at least one of symbols and messages.

22. The endoscope insertion shape detecting device according to claim 14, wherein
the predetermined notification information is information having at least one of symbols and messages.

23. The endoscope insertion shape detecting device according to claim 15, wherein
the predetermined notification information is information having at least one of symbols and messages.

24. The endoscope insertion shape detecting device according to claim 16, wherein
the predetermined notification information is information having at least one of symbols and messages.

* * * * *